March 28, 1939. R. Y. KIMURA Plant Pat. 322
DAHLIA
Filed July 20, 1938
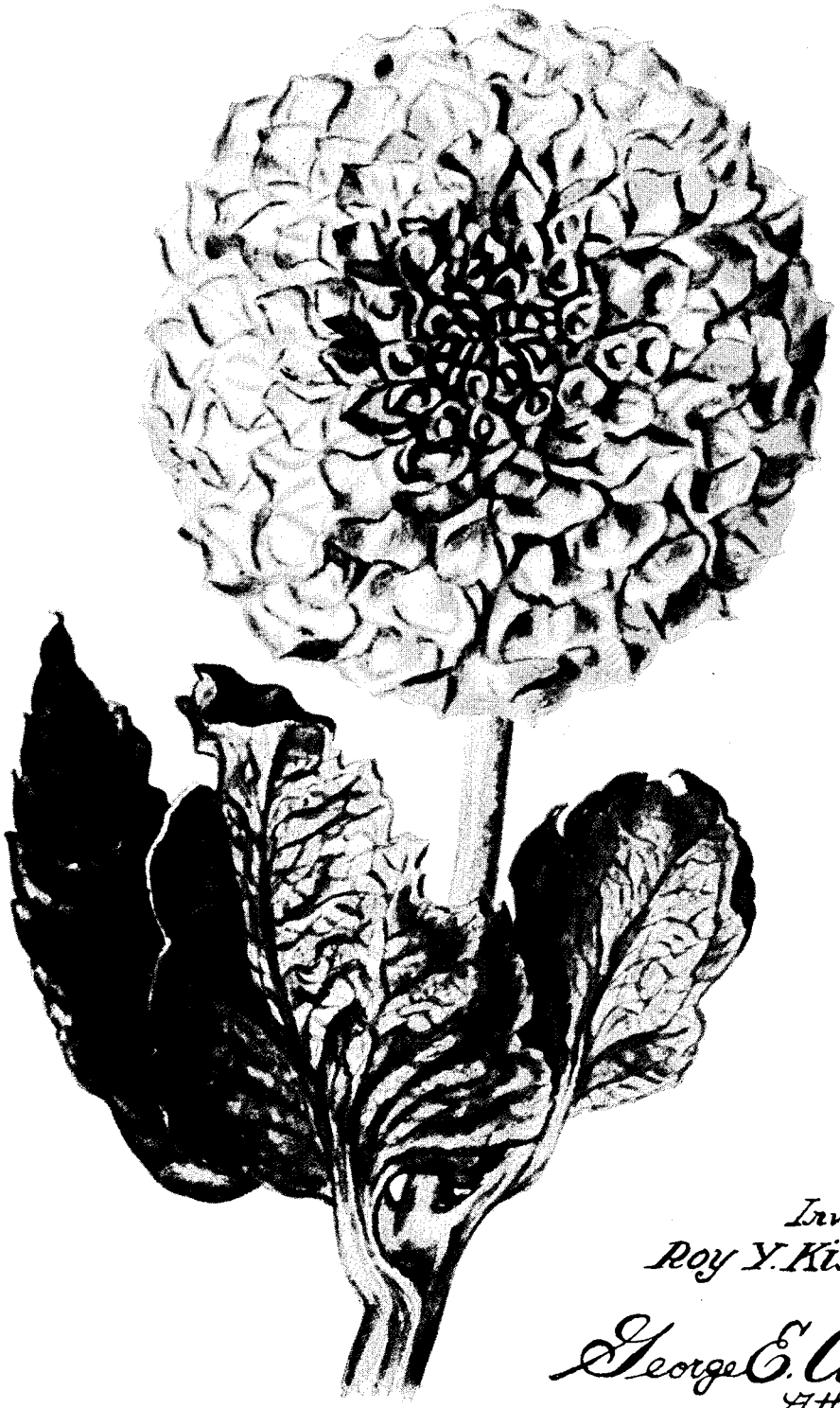
Inventor
Roy Y. Kimura
George E. Cook.
Attorney.

Patented Mar. 28, 1939

Plant Pat. 322

UNITED STATES PATENT OFFICE

322

DAHLIA

Roy Yoshikata Kimura, Los Angeles, Calif.

Application July 20, 1938, Serial No. 220,302

1 Claim. (Cl. 47—60)

My present invention relates to improvements in decorative dahlias and was developed by definite efforts.

After several years of raising dahlias I noticed that red varieties were the best sellers but were conspicuously weak and wilted after about twenty-four hours when used as cut flowers. I therefore began experiments with definite objects in mind, as follows:

First, to produce a variety of distinct red color.

Second, to produce a variety of the "bowl-shaped" type.

Third, to produce a variety of average and uniform size.

Fourth, to produce a variety which lasts longer than the average when used as a cut-flower.

To obtain these results I proceeded as follows:

First I collected seedlings of informal red decorative types of dahlias of many different kinds. These I crossed and recrossed through several generations. I then scientifically selected the best specimens of each type of red dahlia thus produced. The seedlings of these selected specimens were then crossed and recrossed, after which I repeated the process of scientifically selecting the best specimens of each different type of resulting red dahlia. After continuing this process of crossing and recrossing through several more generations, I finally obtained the dahlia which is the subject of the present application.

The new variety has been asexually reproduced by means of division of the roots and has retained its characteristics.

The illustrations accompanying this application show a full front view of one of the blossoms of this new variety, with a portion of the stem and leaves. However, it is impossible for the artist to completely show the brilliance and velvety sheen of this variety.

Following is a detailed description of the plant and flower of this variety. Color plate references are to Ridgway's Color Standards and Nomenclature. Any other color references pertain to the ordinary dictionary definitions.

*The plant*

Growth:

Usually the plant attains a height of from 3 to 4 feet and is very sturdy in growth.

Foliage:

The foliage is abundant on the lower part of the plant but sparse near the flower. It is substantial and rather leathery. The upper surface is Dark Cress Green (Plate XXXI) and the lower surface Pois Green (Plate XLI). However, the upper surface is shiny rather than dull as shown in the color plate.

Stem:

Strong, sturdy and amply able to hold the blossom erect. Smooth and with no foliage for eight or ten inches below the blossom. Liver Brown (Plate XIV) on the side next the sun, gradually blending into the Cress Green (Plate XXXI) of the opposite side of the stem.

*The blossom*

Arrangement:

Like all dahlias, the blossom of this variety is a composite blossom composed of many small flowers forming a disk center and numerous ray flowers extending outward from the disk. Both the disk and ray flowers are arranged in rows separated by rows of bracts. The blossom is of the closed-center, "bowl" type and is very even and symmetrical.

Disk flowers:

There are about 75 disk flowers in the center of a blossom of this variety but they are usually covered by some of the ray flowers. However, as the blossom begins to wither the disk flowers open and expand and usually the entire disk is then visible. The general appearance of the disk flowers is bright yellow, approximately Light Cadmium (Plate IV) with a Lemon Yellow (Plate IV) tip, all encased in a thin membrane of the same color as the bracts. Close examination shows the Lemon Yellow to be the pistil which divides into two branches near the top of the corolla, the latter being about two-thirds the length of the entire pistil. The stamen with its pollen gives the Light Cadmium effect, and the membrane is the corolla-tube, which is a five-lobed tube terminating at the top in five sharp "saw-teeth."

Ray flowers:

This variety averages about 165 ray flowers to the blossom and they are regularly arranged around the disk in close rows between rows of bracts.

*Shape.*—The ray flowers are very even in shape and fall into three classes in the opening flower, each class being uniform. The outer rows spread out rather flat but with even, well-curved edges; the intermediate are involute and form a tubular cup; the inner form a tightly-folded, flat tube pointed at each end. These latter usually open up before the blossom finally withers.

*Size.*—Outer ray flowers are 2¼ to 2½ inches long by 1½ inches wide; intermediate, 1½ inches long by ¾ inch wide in their tubular cup form but 1¼ inches wide when spread out; inner, 1¼ inches long by ⅝ inch wide in their folded form but slightly less than 1 inch wide when spread out.

*Color.*—Ridgway's Color Standards shows no color like the ray flowers of this variety. The nearest for the outer ray flowers falls between Scarlet Red and Spectrum Red (Plate I), although the flower color tends somewhat more to the orange. The under surface is lighter and more nearly Scarlet Red (Plate I) but with the parallel veins having a silvery appearance. Progressing toward the center of the blossom, the ray flowers are somewhat darker in shade. The color in Ridgway's which is nearest the color of the inner ray flowers is Carmine (Plate I), the intermediate ray flowers ranging between the two shades. There is a rich velvety sheen over the entire upper surface of the ray flowers which tends to give the effect of a darker shade.

*Size.*—Medium, averaging about 5½ inches in diameter and 3 to 4 inches in depth.

Bracts:

Rows of bracts separate the rows of flowers of both types, and extend one-third to one-half the length of the flowers themselves. The color is Bright Chalcedony Yellow (Plate XVII). If all the ray flowers are removed from the blossom the effect is that of a yellowish-green flower somewhat similar in appearance to a strawflower and from 2 to 2½ inches in diameter.

Longevity:

Has excellent keeping qualities. Keeps 300 percent longer than the average red dahlia when used as a cut flower.

Having thus disclosed my invention, I claim:

A new variety of dahlia plant as illustrated and described, characterized particularly by its blossoms of distinctive red color, uniform medium size, and symmetrical "bowl-shaped" form with closed center, having unusually good keeping qualities.

ROY YOSHIKATA KIMURA.